United States Patent
Deshpande et al.

(10) Patent No.: US 7,084,307 B2
(45) Date of Patent: Aug. 1, 2006

(54) PROCESS FOR OXIDATION OF ALKANES

(75) Inventors: Raj M. Deshpande, Maharashtra (IN); Makarand M. Diwakar, Maharashtra (IN); Raghunath Vitthal Chaudhari, Maharashtra (IN)

(73) Assignee: Council of Scientific and Industrial Research, New Dehli (IN)

( * ) Notice: Subject to any disclaimer, the term of this patent is extended or adjusted under 35 U.S.C. 154(b) by 24 days.

(21) Appl. No.: 11/019,942

(22) Filed: Dec. 23, 2004

(65) Prior Publication Data
US 2006/0142620 A1    Jun. 29, 2006

(51) Int. Cl.
*C07C 45/33*    (2006.01)
(52) U.S. Cl. .................... 568/399; 568/910; 568/910.5
(58) Field of Classification Search ...................... None
See application file for complete search history.

(56) References Cited

U.S. PATENT DOCUMENTS 5,347,057 A * 9/1994 Khan .......................... 568/910
5,393,922 A * 2/1995 Sen et al. .................... 562/542
5,623,090 A * 4/1997 Haruta et al. ................ 568/360

OTHER PUBLICATIONS

Lin et al. A Highly Catalytic System for the Direct Oxidation of Lower Alkanes by Dioxygen in Aqueous Medium. Journal of the American Chemical Socitey, 1992, vol. 114, p 7307-7308.*

Lin et al. A Highly Catalytic Bimetallic System for the Low-Temperature Selective Oxidation of Methane and Lower Alkanes with Dioxygen as the Oxidant. Journal of the American Chemical Society, 1997, vol. 119, p 6048-6053.*

Rudakov et al. Metallokompleksni Katal., 1977, p 116-129.*

* cited by examiner

*Primary Examiner*—Sikarl A. Witherspoon
(74) *Attorney, Agent, or Firm*—Nixon & Vanderhye P.C.

(57) ABSTRACT

A palladium complex catalyzed process for the oxidation of linear alkanes is proposed which employs molecular oxygen as the oxidant to produce secondary alcohols and ketones in high selectivity, the said catalyst is a single entity and does not requires the use of any co-catalyst or solvent.

13 Claims, No Drawings

PROCESS FOR OXIDATION OF ALKANES

FIELD OF INVENTION

The present invention relates to a process for the oxidation of alkanes to oxygenated hydrocarbons having a formula (1) $R_1$—C(O)—$R_2$ and formula (2) $R_1$—C(OH)—$R_2$ wherein $R_1$, $R_2$ are alkyl groups having a general formula $C_nH_{2n+1}$, where n can be any number between 1 and 23.

The oxygenated hydrocarbons of formula (1) and (2) are prepared from saturated linear hydrocarbons by an oxidation reaction in the presence of molecular oxygen. The catalyst employed for the oxidation reaction is a preformed metal complex of palladium wherein the oxidation state of palladium is (II).

BACKGROUND OF THE INVENTION AND THE PRIOR ART

Oxidation of alkanes is an important reaction for conversion of saturated hydrocarbons to their corresponding alcohols/ketones, which have major applications as plasticizers, solvents, and also as detergent grade alcohols in the production of biodegradable surfactants.

The use of palladium metal and palladium organometallic complexes for alkane oxidation are well known. A majority of literature reports on palladium catalyzed oxidation deals with lower alkane oxidation ranging from methane to butane using molecular oxygen, in a highly acidic medium. Reference is made to the paper, Metallokompleksnyi Katal., 116–29, 1977 by Rudakov et al. wherein the oxidation of saturated hydrocarbons is reported using palladium(II) complexes as catalysts in highly acidic media like sulfuric acid, sulfuric acid-aluminum sulfate, and phosphoric acid-boron trifluoride. The disadvantage of this system is the essential requirement of a highly acidic medium, to conduct the reaction, which is avoided in the present new process. The present invention can be conducted without any solvent, and hence is devoid of any acidic/corrosive components.

Reference is be made to a paper Struktura, Reaktsion. Sposobnost Organ Soedin i Mekhanizmy Reaktsii, Kiev, 69–101 From: Ref Zh., Khim. 1981, Abstr. No. 11B1095, 1980, to Rudakov et al., wherein the oxidation of linear alkane is carried out using palladium sulfate, and nitronium ions in a 80–100% sulfuric acid medium. The oxidant used in this system is nitronium ion. The present invention employs molecular oxygen as an oxidant.

Reference is made to another paper, New J. Chem., 13(10–11), 761–6, 1989, by Herron et al., wherein zeolite supported Fe/Pd bimetallic catalysts are used for the selective oxidation of alkanes at room temperature. Here a mixture of hydrogen and oxygen, or $H_2O_2$ is used as an oxidant. In contrast, the present invention employs molecular oxygen as the oxidant in the presence of a Pd(II) complex. No hydrogen or other sacrificial reductant is required.

Reference is also made to a publication in, J. Am. Chem. Soc., 1114(18), 7307–8, by Lin et al., wherein Pd metal is used to catalyze methane oxidation by molecular oxygen in aqueous medium at 70°–110° to $HCO_2H$. Ethane oxidation to acetic acid and formic acid is also observed in the presence of the same catalyst. In this report, the catalyst used is palladium metal in an aqueous medium, whereas, in the present invention the catalyst used is necessarily a Pd(II) complex. In addition in the present invention, solvent is not an essential requirement as the reaction can be conducted with pure substrate.

Reference is made to the paper in, J. Am Chem. Soc., 119(26), 6048–6053, 1997, by Lin et al., wherein a bimetallic Palladium and Copper chloride catalyst is used for low-temperature oxidation of methane, ethane, and butane to corresponding acids and alcohols in the presence of dioxygen and carbon monoxide. The presence of Copper is essential to reoxidize Palladium. The reaction medium used is strongly acidic—aqueous trifluoroacetic acid. In contrast, the present invention employs Pd(II) complex catalyst in a reaction medium devoid of any acid, and does not require any co-catalyst.

U.S. Pat. No. 5,623,090 to Masatake et al., discloses the use of gold particles deposited on titanium dioxide carrier as an oxidation catalyst. This catalyst is reported to catalyze the oxidation of saturated hydrocarbons to alcohols and ketones in the presence of molecular oxygen. In the present invention, the catalyst used is a Pd(II) complex catalyst, and not $Au/TiO_2$.

U.S. Pat. No. 5,235,117, to Jacques et al., reports the preparation of boric acid and its use in the oxidation of saturated hydrocarbons to alcohols. In the present invention the oxidation catalyst used is Pd(II) complex catalyst which catalyses the alkane oxidation in the presence of molecular oxygen No boric acid is employed in the present invention.

Palladium(II) acetate is used to effect the trifluoroacetoxylation of alkanes such as adamantane and methane as well as, arenes in trifluoroacetic acid, as reported in New J. Chem., 13(10–11), 755–60, 1989, to Sen et al., The reaction is made catalytic in Pd(IT) by the addition of a cooxidant, $K_2S_2O_8$, which reoxidizes the $Pd^0$ formed at the end of the trifluoroacetoxylation step. In the present invention Pd(II) metal complex is used as a catalyst and it does not require any cooxidant to carry out the oxidation reaction.

PCT Publication WO 9214738 A1, to Periana et al, wherein $PdSO_4.2\ H_2O$ is used as a catalyst to convert methane to $MeOSO_3H$ in 20% oleum at 100° C. In this report use of $PdSO_4$ as an oxidation catalyst for oxidation of methane to esters and alcohols in highly acidic medium is also reported. In present invention, the catalyst used is Pd(II) complex and the reaction is carried out in acid free solvent and with a pure substrate.

Supported palladium metal is also used for the oxidation of alkanes as reported by Haack et al in Catal. Lett., 34(1,2), 31–40, 1995, wherein Pd/□-alumina and Pd foil is used for methane oxidation, Appl Catal., B, 9(1–4), 251–266, 1996, by Maillet et al., wherein $Pd/Al_2O_3$ catalyst is reported for the oxidation of propane in exhaust gas under steam and oxygen/steam system, and in yet another paper by Muto et al., in Catal Today, 35(1–2), 145–151, 1997, wherein alumina coated with a monolayer of palladium loaded silica is reported for oxidation of methane. In the paper by Mazza et al., in Riv. Combust., 50(11–12), 439–443, 1996, palladium loaded titania catalyst is used for oxidation of linear paraffin, n-hexane. ($PdCl_2$-heteropoly acid)/$SiO_2$ system is used for the oxidation of n-$C_4H_{10}$, n-$C_5H_{12}$ at 300° C. in Kinet. Catal. (Transl of Kinet. Katal.), 36 (3), 373–6, 995 by Volkova et al., where as in the present invention the catalyst used is not Pd in metallic state and is also not supported on any inert support. The present invention uses a non supported Pd(II) metal complex.

From the prior art it is clear that the studies relate mainly to oxidation of lower alkanes/cycloalkanes using heterogeneous, supported Pd catalysts, in the presence of a co-catalysts or co-oxidants or in the presence of a reductant like $H_2$ or CO.

These drawbacks are obviated in the present invention, which employs an organometallic Pd complex catalyst, using molecular oxygen as the reactant, in the absence of any co-catalyst or any acidic solvent. In fact the present invention can also be practiced in the absence of any solvent.

OBJECT OF THE INVENTION

The object of the present invention is to provide a process for the oxidation of alkanes, which obviates the drawbacks as detailed above.

SUMMARY OF THE INVENTION

Accordingly the present invention provides a process for oxidation of alkanes of formula $C_nH_{2n+2}$, which comprises reacting an alkane with oxygen in presence of a palladium complex catalyst of the formula $Pd^{II}L_1L_2L_3L_4$ wherein $L_1$, $L_2$, $L_3$, $L_4$ are identical or different and are selected from the group consisting of monodentate, bidentate, polydentate ligands and derivatives thereof, such that the maximum number of coordination for Palladium is 4, to obtain a mixtures of alcohols and ketones corresponding to the alkane used.

In one embodiment of the invention, the monodentate, bidentate, polydentate ligands and derivatives thereof are selected from the group consisting of alkyl, aryl and alkylaryl phosphines, diphosphines, alkyl, aryl and alkylaryl amines, diamines, nitrogen containing heterocyclic and substituted heterocyclic ligands, pyridines, bipyridines, phenanthrolines, bathophenanthrolines, phthalocynines, Schiff base ligands derived from salicylaldehyde—diamines, salicylaldehyde—monoamines, halogen and organic acid anions.

In another embodiment of the invention, the reaction is carried out at a temperature in the range of 50 to 250° C., and at a pressure in the range of 1 psi to 2000 psi oxygen.

In another embodiment of the invention, the reaction is carried out in the presence of gaseous diluents or air.

In another embodiment of the invention, the reaction is carried out for at least 15 minutes.

In another embodiment of the invention, the reaction is carried out in the presence of a solvent.

In a further embodiment of the invention, the solvent is selected from the group consisting of acetonitrile, secondary or primary or tertiary alkyl alcohols and dialkyl ketones.

In another embodiment the reaction is carried out in the absence of a solvent.

In another embodiment the alkane is selected from the group consisting of $C_3$ to $C_{24}$ alkanes and is used singly or as a mixture of alkanes.

In yet another embodiment the reaction is carried out using pure oxygen.

In another embodiment the reaction is carried out in the presence of diluted oxygen with inert gases selected from the group consisting of nitrogen, helium and argon, or in presence of air.

In another embodiment the reaction is carried out using a continuous stream of the gas selected from the group consisting of oxygen, air, or oxygen diluted with nitrogen or air.

In yet another embodiment the reaction takes place at atmospheric or above atmospheric pressure with continuous feeding of the reactant oxygen commensurate with the consumption thereof.

DETAILED DESCRIPTION OF THE INVENTION

The present invention provides a process for the oxidation of alkanes having formula $C_nH_{2n+2}$. The process comprises reacting an alkane with oxygen in the presence of a palladium complex catalyst of the type $Pd^{II}L_1L_2L_3L_4$ wherein $L_1$, $L_2$, $L_3$, $L_4$ are identical or different, monodentate, bidentate or polydentate ligands such that the maximum number of coordination for Palladium is 4. The reaction is effected at a temperature in a range of 50 to 250° C., at a pressure in the range of 1 psi to 2000 psi oxygen, optionally in the presence of gaseous diluents or air, and optionally in the presence of a solvent, for at least 15 minutes to obtain a mixtures of alcohols and ketones corresponding to the alkane used.

The ligands used are monodentate, bidentate or polydentate ligands or their derivatives selected from alkyl, aryl and alkylaryl phosphines, diphosphines, alkyl, aryl and alkylaryl amines, diamines, Nitrogen containing heterocyclic and substituted heterocyclic ligands, pyridines, bipyridines, phenanthrolines, bathophenanthrolines, phthalocynines, Schiff base ligands derived from salicylaldehyde—diamines, salicylaldehyde—monoamines, halogen, organic acid anions.

The reaction is conducted in the presence of a solvent comprising of acetonitrile, secondary or primary or tertiary alkyl alcohols and dialkyl ketones or in the absence of any solvent. The alkane varies from $C_3$ to $C_{24}$, and is used either singly or as a mixture of alkanes.

The reaction is carried out using pure oxygen or in the presence of diluted oxygen, wherein the other components are inert gases like nitrogen, helium, argon or in presence of air. The reaction may preferably be carried out using a continuous stream of the gas, which can be oxygen, air, or oxygen diluted with nitrogen or air. The reaction is taken at atmospheric or above atmospheric pressure with continuous feeding of the reactant oxygen commensurate with the consumption.

The process of the present invention is described hereinbelow with reference to the illustrative examples, which should not be construed to limit the scope of the present invention in any manner whatsoever.

EXAMPLE-1

Example 1 describes the preparation of a typical catalyst complex starting from Pd salt and ligand. This is a representative example and can be extended to preparation of metal complexes of palladium using palladium salts of halides, and organic acids and other ligands containing the amine moiety.

The palladium complex $PdCl_2Bipy$ was prepared as follows: 0.0030 mole 2,2'-bipyridine was taken in 10 ml methanol and to it 0.0029 mole $PdCl_2$ was added. The mixture as stirred for 6 hrs at room temperature. The resulting yellowish red coloured precipitate as filtered washed with methanol and dried under vacuum. The yield of the complex is 85%.

EXAMPLE 2

A 50 ml round bottom flask equipped with reflux condenser and thermowell was charged with 0.0171 mole hexadecane and $8.018 \times 10^{-5}$ mole $PdCl_2Bipy$. The $PdCl_2Bipy$ complex was prepared using standard procedure as given in example 1. The round bottom flask was then flushed with $O_2$ and heated to 140° C. in an oil bath. The reaction mixture was stirred for 16 hours using magnetic stirrer under oxygen blanket provided by a balloon under slightly positive pressure. At the end of reaction the contents were cooled to room temperature. Whole reaction mixture was diluted with tetrahydrofuran and this solution was then analysed using gas chromatography. Analysis of reaction mixture showed 17.28% conversion of hexadecane, with 36.65% selectivity to $C_{16}$ ketones (hexadecanones), and 40.42% selectivity to $C_{16}$ secondary alcohols (secondary hexadecanols).

EXAMPLE-3

Pd(OAc)$_2$Bipy complex was prepared using standard procedure as given below 0.0030 mole 2,2'-bipyridine was taken in a 10 ml methanol and to it 0.0029 mole Pd(OAc)$_2$ was added. The mixture was stirred for 6 hrs at room temperature. The yellow coloured precipitate was filtered washed with methanol and dried under vacuum. The yield of the complex is 89%.

EXAMPLE-4

A 50 ml round bottom flask equipped with reflux condenser and thermowell was charged with 0.0171 mole hexadecane and 8.018×10$^{-5}$ mole Pd(OAc)$_2$Bipy. The round bottom flask was then flushed with O$_2$ and heated at 140° C. The reaction mixture was stirred for 16 hours using magnetic stirrer under oxygen blanket provided by a balloon under slightly positive pressure. At the end of reaction the contents were cooled to room temperature. The whole reaction mixture was diluted with tetrahydrofuran and this solution was then analysed using gas chromatography. Analysis of the reaction mixture showed 23.88% conversion of hexadecane, with 32.3% selectivity to $C_{16}$ ketones (hexadecanones), and 39.4% selectivity to $C_{16}$ secondary alcohols (secondary hexadecanols)

EXAMPLE-5

A reaction was conducted to check recyclability of the catalyst. A 50 ml round bottom flask equipped with reflux condenser and thermowell was charged with 0.0171 mole hexadecane and 8.018×10$^{-5}$ mole PdCl$_2$Bipy. The PdCl$_2$Bipy complex was prepared Jsing standard procedure as given in example-1. The round bottom flask was then flushed with O$_2$ and heated at 140° C. The reaction mixture was stirred for 16 hours using magnetic stirrer under oxygen blanket provided by a balloon under slightly positive pressure. At the end of reaction the contents were cooled to room temperature. The catalyst was filtered and washed with pet ether (3×5 ml), and dried under vacuum. The reaction mixture was diluted with tetrahydrofuran and this solution was then analysed using gas chromatography. Analysis of the reaction mixture showed 17.28% conversion of hexadecane, with 36.65% selectivity to $C_{16}$ ketones (hexadecanones), and 40.42% selectivity to $C_{16}$ secondary alcohols (secondary hexadecanols). The catalyst filtered from reaction was taken in a 50 ml round bottom flask equipped with reflux condenser and thermowell. The round bottom flask was charged with 0.0171 mole hexadecane. The round bottom flask was then flushed with O$_2$ and heated at 140° C. The reaction mixture was stirred for 16 hours using magnetic stirrer under oxygen blanket provided by a balloon under slightly positive pressure. At the end of reaction the contents were cooled to room temperature. The reaction mixture was diluted with tetrahydrofuran and this solution was then analysed using gas chromatography. Analysis of the reaction mixture showed 19.23% conversion of hexadecane, with 33.34% selectivity to $C_{16}$ ketones (hexadecanones), and 42.31% selectivity to $C_{16}$ secondary alcohols (secondary hexadecanols).

EXAMPLE-6

A 50 ml round bottom flask equipped with reflux condenser and thermowell was charged with 0.0171 mole decane and 8.018×10$^{-5}$ mole PdCl$_2$Bipy. The PdCl$_2$Bipy complex was prepared using standard procedure as given in example-1. The round bottom flask was then flushed with O$_2$ and heated at 140° C. The reaction mixture was stirred for 16 hours using magnetic stirrer under oxygen blanket provided by a balloon under slightly positive pressure. At the end of reaction the contents were cooled to room temperature. The reaction mixture was diluted with tetrahydrofuran and this solution was then analysed using gas chromatography. Analysis of the reaction mixture showed 14.71% conversion of decant, with 32.04% selectivity to $C_{10}$ ketones (decanones), and 39.22% selectivity to $C_{10}$ secondary alcohols (secondary decanols).

EXAMPLE-7

A 50 ml round bottom flask equipped with reflux condenser and thermowell was charged with 0.0171 mole dodecane and 8.018×10$^{-5}$ mole PdCl$_2$Bipy. The PdCl$_2$Bipy complex was prepared using standard procedure as given in example-1. The round bottom flask was then flushed with O$_2$ and heated at 140° C. The reaction mixture was stirred for 16 hours using magnetic stirrer under oxygen blanket provided by a balloon under slightly positive pressure. At the end of reaction the contents were cooled to room temperature. The reaction mixture was diluted with tetrahydrofuran and this solution was then analysed using gas chromatography. Analysis of the reaction mixture showed 17.90% conversion of dodecane, with 34.04% selectivity to $C_{12}$ ketones (dodecanones) and 39.57% selectivity to $C_{12}$ secondary alcohols (secondary dodecanols)

EXAMPLE-8

A 50 ml round bottom flask equipped with reflux condenser and thermowell was charged with 0.0171 mole hexadecane and 0.170 g 5% Pd on carbon. The 5% Pd on carbon was procured from Precious Metal Products, ARORA MATTHEY LIMITED. The round bottom flask was then flushed with O$_2$ and heated at 140° C. The reaction mixture was stirred for 16 hours using magnetic stirrer under oxygen blanket provided by a balloon under slightly positive pressure. At the end of reaction the contents were cooled to room temperature. The reaction mixture was diluted with tetrahydrofuran and this solution was then analyzed using gas chromatography. Analysis of the reaction mixture showed no conversion of hexadecane.

EXAMPLE-9

A 50 ml round bottom flask equipped with reflux condenser and thermowell was charged with 0.0171 mole hexadecane and 0.85 g 1% Pd on carbon. The 1% Pd on carbon was procured from John Baker Inc. Colorado USA. The round bottom flask was then flushed with O$_2$ and heated at 140° C. The reaction mixture was stirred for 16 hours using magnetic stirrer under oxygen blanket provided by a balloon under slightly positive pressure. At the end of reaction the contents were cooled to room temperature. The reaction mixture was diluted with tetrahydrofuran and this solution was then analysed using gas chromatography. Analysis of the reaction mixture showed no conversion of hexadecane.

Examples 8 and 9 show that Pd/C catalyst is not active for the reaction.

EXAMPLE-10

The (Pd- ethylene diamine-salicylaldehyde) complex was prepared using following procedure. All experimental work was carried out under inert atmosphere. To a flask containing 15 ml methanol 0.5 ml salicylaldehyde was added, to it 0.16 ml ethylene diamine was added under constant stirring. The mixture was refluxed for 30 mins. To this 0.43 g $PdCl_2$ was added and the mixture was stirred for 4 hrs at room temperature. The yellow coloured material was filtered and washed with methanol and then dried under vacuum.

EXAMPLE-11

A 50 ml round bottom flask equipped with reflux condenser and thermowell was charged with 0.0171 mole hexadecane and $8.018 \times 10^{-5}$ mole (Pd-ethylene diamine-salicylaldehyde). The Pd-salen complex was prepared using standard procedure as given in example-10. The round bottom flask was then flushed with $O_2$ and heated to 140° C. in an oil bath. The reaction mixture was stirred for 16 hours using magnetic stirrer under oxygen blanket provided by a balloon under slightly positive pressure. At the end of reaction the contents were cooled to room temperature. The whole reaction mixture was diluted with tetrahydrofuran and this solution was then analysed using gas chromatography. Analysis of the reaction mixture showed 17.28% conversion of hexadecane, with 36.65% selectivity to $C_{16}$ ketones (hexadecanones), and 40.42% selectivity to $C_{16}$ secondary alcohols (secondary hexadecanols).

EXAMPLE-12

A 25 ml glass reactor equipped with reflux condenser, thermowell and gas bubbler was charged with 0.05 mole hexadecane and $8.018 \times 10^{-5}$ mole $PdCl_2Bipy$. The $PdCl_2Bipy$ complex was prepared using standard procedure as given in example-1. The glass reactor was then heated at 140° C. using oil bath and oxygen was bubbled through it at the rate of 0.5 ml per minute. The reaction was carried out for five hours. At the end of reaction the contents were cooled to room temperature. The reaction mixture was diluted with tetrahydrofuran and this solution was then analysed using gas chromatography. Analysis of the reaction mixture showed 26.00% conversion of hexadecane, with 35.47% selectivity to $C_{16}$ ketones (hexadecanones), and 49.65% selectivity to $C_{16}$ secondary alcohols (secondary hexadecanols).

EXAMPLE-13

A 50 ml autoclave equipped with magnetic stirrer, automatic temperature controller. The reactor was charged with 0.05 mole hexadecane and $1.60 \times 10^{-4}$ mole $PdCl_2Bipy$. The $PdCl_2Bipy$ complex was prepared using standard procedure as given in example-1. The reactor was flushed with 5% $O_2$ in $N_2$ and pressurized up to 1200 psig at room temperature. The reactor was then heated to 120° C. under stirring. The reactor temperature increased to 150° C. after attaining 120° C. temperature and then decreased to 120° C. gradually. The reactor was then cooled to room temperature and discharged after venting the gas. The reaction mixture was diluted with tetrahydrofuran and this solution was then analysed using gas chromatography. Analysis of the reaction mixture showed 31.51% conversion of hexadecane, with 35.49% selectivity to $C_{16}$ ketones (hexadecanones) and 54.86% selectivity to $C_{16}$ secondary alcohols (secondary hexadecanols).

From these examples it is clear that the oxidation of alkanes using molecular oxygen is feasible in the presence of palladium complex catalysts of the type mentioned above, to yield secondary alcohols and ketones.

The main advantages of the present invention are:

Selective direct oxidation of linear alkanes using molecular oxygen

Non-corrosive and uncomplicated system comprising of single catalyst component, heterogeneous in nature and easily recyclable No co-catalyst or promoter is required, Reaction can be conducted in absence of solvents and hence is ecofriendly

We claim:

1. A process for oxidation of alkanes of formula $C_nH_{2n+2}$, which comprises reacting an alkane with oxygen in presence of a palladium complex catalyst of the formula $Pd_nL_1L_2L_3L_4$ wherein $L_1$, $L_2$, $L_3$, $L_4$ are identical or different and are selected from the group consisting of monodentate, bidentate, polydentate ligands and derivatives thereof, such that the maximum number of coordination for Palladium is 4, to obtain a mixtures of alcohols and ketones corresponding to the alkane used.

2. A process as claimed in claim 1 wherein the monodentate, bidentate, polydentate ligands and derivatives thereof are selected from the group consisting of alkyl, aryl and alkylaryl phosphines, diphosphines, alkyl, aryl and alkylaryl amines, diamines, nitrogen containing heterocyclic and substituted heterocyclic ligands, pyridines, dines, phenanthrolines, bathophenanthrolines, phthalocynines, Schiff base ligands derived from salicylaldehyde—diamines, salicylaldehyde—monoamines, halogen and organic acid anions.

3. A process as claimed in claim 1 wherein the reaction is carried out at a temperature in the range of 50 to 250° C., and at a pressure in the range of 1 psi to 2000 psi oxygen.

4. A process as claimed in claim 1 wherein the reaction is carried out in the presence of gaseous diluents or air.

5. A process as claimed in claim 1 wherein the reaction is carried out for at least 15 minutes.

6. A process as claimed in claim 1 wherein the reaction is carried out in the presence of a solvent.

7. A process as claimed in claim 6 wherein the solvent is selected from the group consisting of acetonitrile, secondary or primary or tertiary alkyl alcohols and dialkyl ketones.

8. A process as claimed in claim 1 wherein the reaction is carried out in the absence of a solvent.

9. A process as claimed in claim 1 wherein the alkane is selected from the group consisting of $C_3$ to $C_{24}$ alkanes and is used singly or as a mixture of alkanes.

10. A process as claimed in claim 1 wherein the reaction is carried out using pure oxygen.

11. A process as claimed in claim 1 wherein the reaction is carried out in the presence of diluted oxygen with inert gases selected from the group consisting of nitrogen, helium and argon, or in presence of air.

12. A process as claimed in claim 1 wherein the reaction is carried out using a continuous stream of the gas selected from the group consisting of oxygen, air, or oxygen diluted with nitrogen or air.

13. A process as claimed in claim 1 wherein the reaction takes place at atmospheric or above atmospheric pressure with continuous feeding of the reactant oxygen commensurate with the consumption thereof.

* * * * *